United States Patent [19]
Vendrely et al.

[11] Patent Number: 5,683,397
[45] Date of Patent: Nov. 4, 1997

[54] DISTAL FEMORAL CUTTING GUIDE APPARATUS FOR USE IN KNEE JOINT REPLACEMENT SURGERY

[75] Inventors: Tim Vendrely, Memphis, Tenn.; Leo A. Whiteside, Bridgeton, Mo.; Thomas A. Carls, Memphis, Tenn.; John Steele, Aurora, Colo.; Chris E. Johnson, Memphis, Tenn.

[73] Assignee: Smith & Nephew, Inc., Memphis, Tenn.

[21] Appl. No.: 389,099

[22] Filed: Feb. 15, 1995

[51] Int. Cl.⁶ .................................................. A61B 17/56
[52] U.S. Cl. .................................................. 606/88
[58] Field of Search .......................... 606/88, 89, 87, 606/86, 96, 80, 82, 79, 102

[56] References Cited

U.S. PATENT DOCUMENTS

| | | |
|---|---|---|
| 4,464,729 | 8/1984 | Mlynek . |
| 4,467,801 | 8/1984 | Whiteside . |
| 4,474,177 | 10/1984 | Whiteside . |
| 4,487,203 | 12/1984 | Androphy . |
| 4,567,886 | 2/1986 | Petersen . |
| 4,703,751 | 11/1987 | Pohl . |
| 4,721,104 | 1/1988 | Kaufman et al. . |
| 4,722,330 | 2/1988 | Russell et al. . |
| 4,736,737 | 4/1988 | Fargie et al. . |
| 4,738,253 | 4/1988 | Buechel et al. . |
| 4,738,254 | 4/1988 | Buechel et al. . |
| 4,759,350 | 7/1988 | Dunn et al. . |
| 4,773,407 | 9/1988 | Petersen . |
| 4,892,093 | 1/1990 | Zarnowski et al. ............ 606/82 |
| 4,893,619 | 1/1990 | Dale et al. ............ 606/87 |
| 4,907,578 | 3/1990 | Petersen ............ 606/79 |
| 4,935,023 | 6/1990 | Whiteside et al. ............ 606/88 |
| 4,952,213 | 8/1990 | Bowman et al. ............ 606/79 |
| 4,959,066 | 9/1990 | Dunn et al. ............ 606/89 |
| 5,002,545 | 3/1991 | Whiteside et al. ............ 606/80 |
| 5,108,405 | 4/1992 | Mikhail et al. ............ 606/96 |
| 5,129,909 | 7/1992 | Sutherland ............ 606/88 |
| 5,454,816 | 10/1995 | Ashby ............ 606/88 |

FOREIGN PATENT DOCUMENTS

| | | |
|---|---|---|
| 0 122 669 | 10/1984 | European Pat. Off. . |
| 340176 | 11/1989 | European Pat. Off. . |
| 466659 | 1/1992 | European Pat. Off. . |

OTHER PUBLICATIONS

Smith & Nephew Richards Genesis™ Total Knee System Catalog (Sep. 1992).

*Primary Examiner*—Guy V. Tucker
*Attorney, Agent, or Firm*—Pravel, Hewitt, Kimball & Krieger

[57] ABSTRACT

A distal femoral cutting block apparatus for use in knee surgery includes an instrument body that has generally flat opposing parallel surfaces and a plurality flat peripheral surfaces to form a generally rectangular body. The body provides anterior and posterior surfaces and medial and lateral surfaces. The transverse slot carries a valgus module that is movably disposed in the slot. The valgus module includes a tubular sleeve member having a pair of opposed sides that abut the body at the slot. A portion of the tubular sleeve member is threaded and the threaded portion extends away from the body. An open ended bore extends through the tubular member. The open ended bore of the tubular sleeve member of the module accommodates an intramedullary rod that fits the patient s intramedullary canal. A lock nut engages the threaded section of the module for locking the module in a desired position on the cutting block body by engaging the threaded portion and the instrument body to rigidly affix them together.

16 Claims, 10 Drawing Sheets

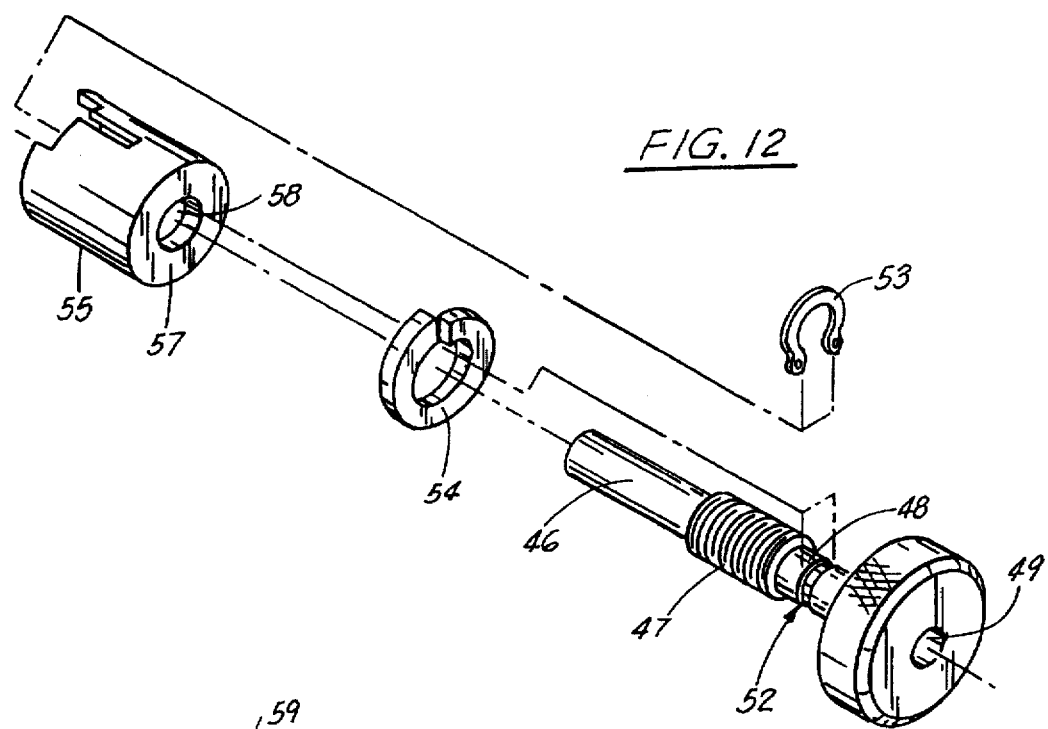
FIG. 12
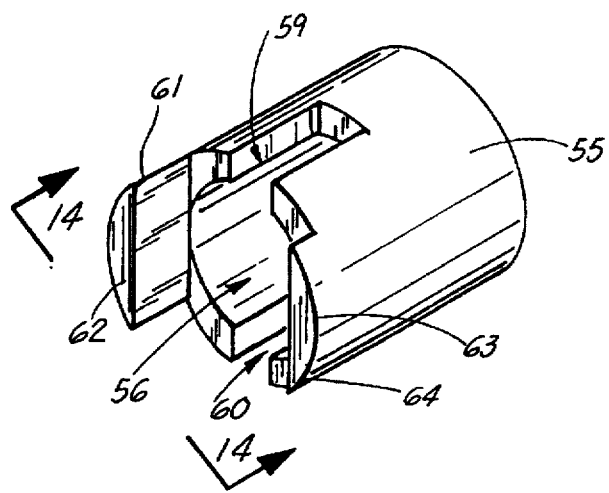
FIG. 13
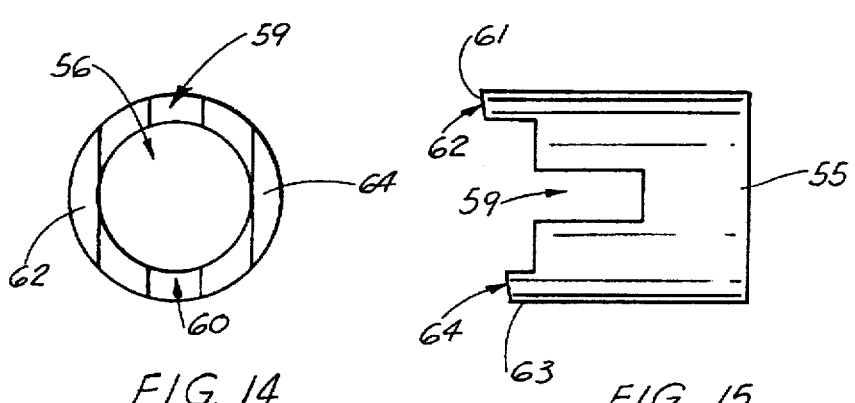
FIG. 14
FIG. 15

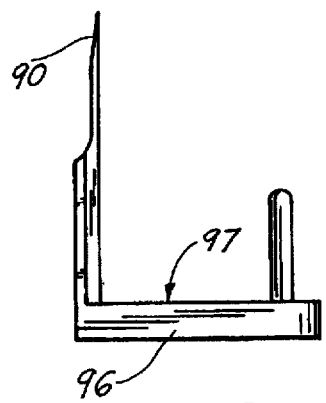
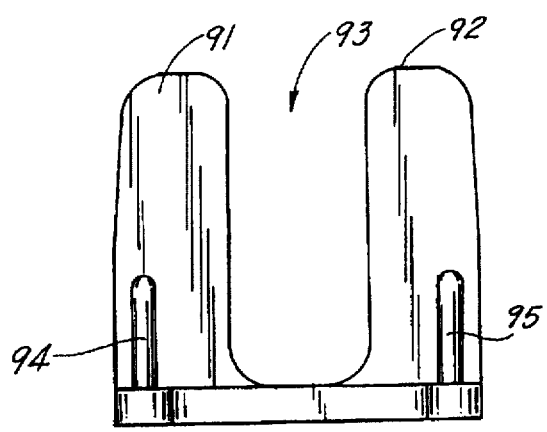
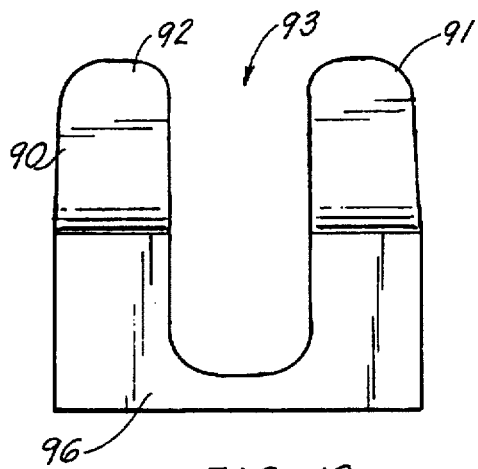
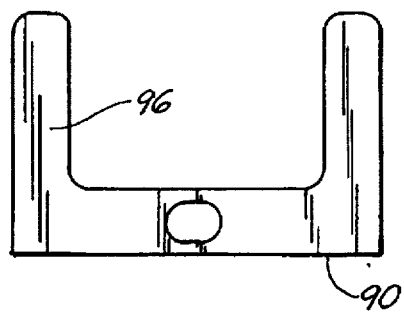
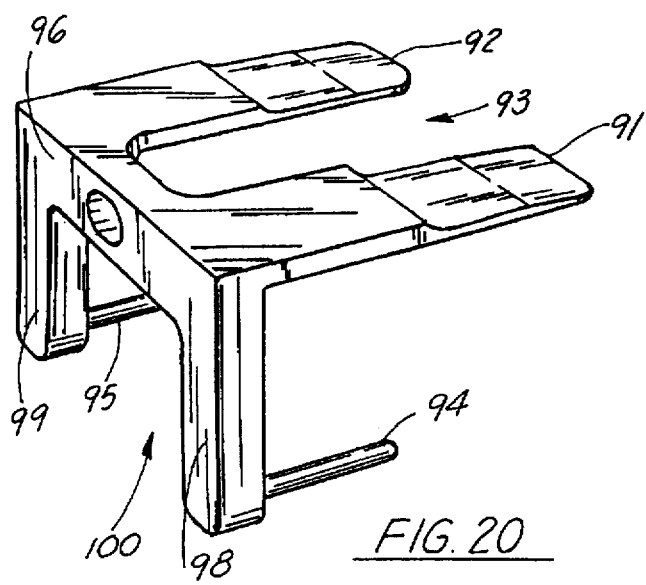
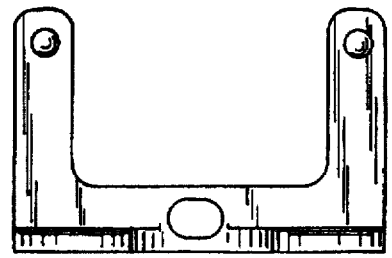

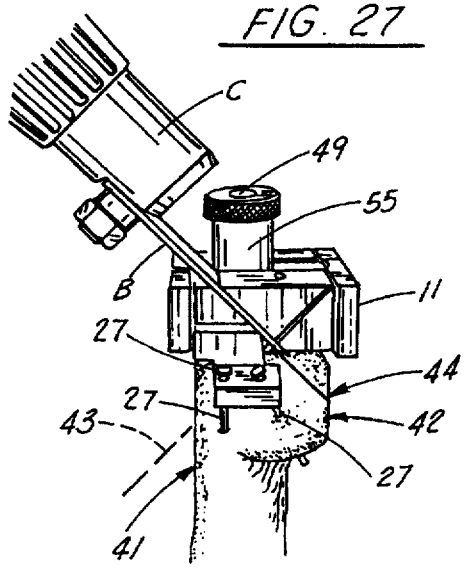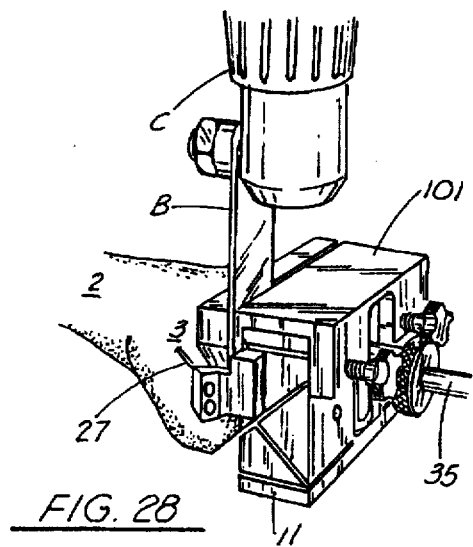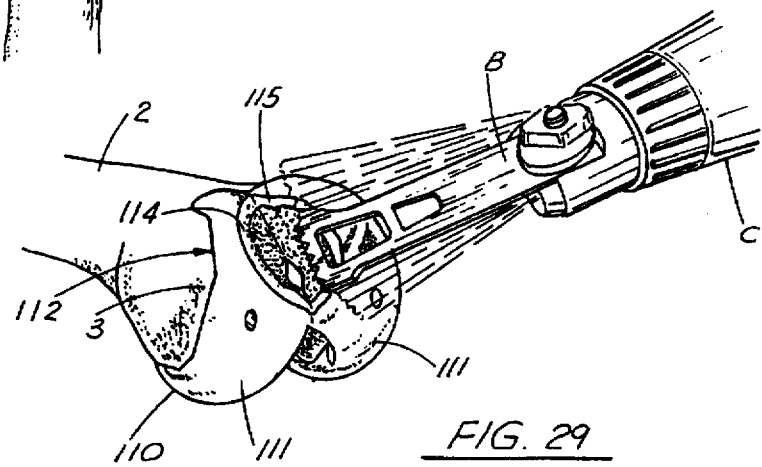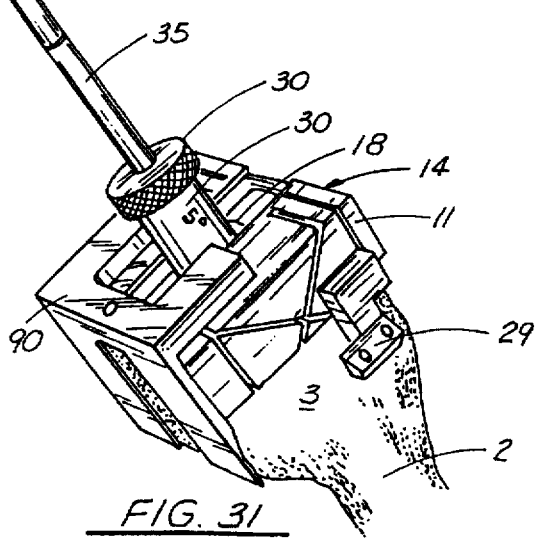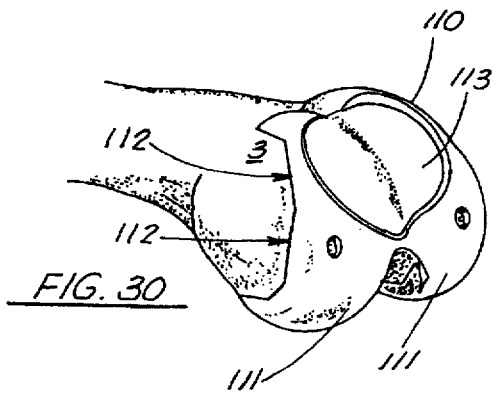

DISTAL FEMORAL CUTTING GUIDE APPARATUS FOR USE IN KNEE JOINT REPLACEMENT SURGERY

BACKGROUND OF THE INVENTION

1. Field of the Invention

The present invention relates to surgical orthopedic cutting instruments, and more particularly relates to an improved cutting block apparatus for shaping the distal femur of a patient prior to the placement of a knee joint prosthesis. Even more particularly, the present invention relates to a distal femoral cutting block apparatus wherein the block carries a valgus module in a slot, the module being adjustably movable into a number of different positions relative to the block and rigidly affixable in a selected position by means of an anchoring mechanism that rides with the block. The valgus module has a bore that fits an elongated reamer mounted in the patient s intramedullary canal and corrects for the valgus angle.

2. General Background

In knee joint replacement surgery, the surgeon often replaces the distal femoral surface of the patient s knee with a metallic prosthesis having a highly polished distal articulating surface that is curved or J-shaped. The femoral prosthesis has a generally smooth continuous outer curvature that faces a corresponding tibial component attached to the patient s proximal tibia.

Common femoral components of a knee prosthesis provide five proximal intersecting flat surfaces that interface with the surgically prepared distal femoral surface. One of the surfaces is adapted to engage the anterior cortical surface of the femur. Another of the flat surfaces is adapted to face the posterior surface of the femur. Yet another surface is adapted to engage the distal end of the patient s femur. Additionally, a pair of chamfer surfaces form diagonally extending surfaces which form an interface between the distal surface and the respective anterior and posterior surfaces of the surgically prepared femur.

A surgeon typically forms five (5) separate cuts on the patient s distal femur in order to prepare the distal femur to receive the femoral prosthesis. One of the problems facing the surgeon is the proper placement of the cuts so that the prosthesis will fit the femur with the correct orientation. One method of orienting a cutting guide is to reference that cutting guide to a rod that is placed in the patient s intramedullary canal.

U.S. Pat. No. 4,474,177 is an example of a cutting block instrument that references a cutting guide to an intramedullary rod that is positioned in the patient s intramedullary canal of the femur.

Before beginning a cutting operation, the surgeon wants to orient the cutting guide in anterior and posterior directions relative to the patient s femur and also relative to the valgus angle of the patient s femur. The present invention provides an improved cutting block apparatus that provides adjustments in all directions before the block is ever anchored to the patient s distal femur and including anterior and posterior adjustment and valgus angle adjustment.

A number of patents have issued which disclose medical cutting instruments for use by orthopedic surgeons. Some of these cutting instruments relate to shaping of the distal femur or adjacent bone structure.

The Whiteside U.S. Pat. No. 4,467,801, entitled Method And Apparatus For Shaping A Proximal Tibial Surface, provides a method and apparatus for preparing the proximal surface of a tibia to receive a proximal tibial prosthesis employing a reamer/alignment guide which is used to internally locate the central long axis of the tibia and a plateau planar which cooperatively engages with a guide handle attached to the reamer/alignment guide to accomplish the shaping of the proximal tibial surface. The reamer/alignment guide has a rod portion extending into the interior of the tibial shaft whose central long axis corresponds with the central long axis of the tibia. The guide handle is concentric with that rod portion such that the plateau planar assumes the proper alignment with respect to the central long axis of the tibia such that the proximal tibial surface is shaped relative to that axis in a simple and accurate manner.

European Patent Application No. 0 122 669 discloses a guide for femoral neck osteotomy that comprises a longitudinal rod having attaching structure at the lower end thereof for securing the rod to a femur at the greater trochanter. A transversely extending support arm is secured to the rod adjacent the lower end thereof, and a guide bar is connected to the support arm. The guide bar has at least one elongated planar surface disposed at an angle of 45° to the axis of the rod. In use, the rod is aligned with the long shaft axis of the femur and attached to the femur at the greater trochanter. The rod is manipulated until the support arm and the long shaft axis of the tibia are disposed in the same plane. This procedure properly positions the elongated planar surface of the guide bar whereby an instrument in engagement with that surface traverses the femoral neck at an angle of 45° to the long shaft axis of the femur.

Another Whiteside U.S. Pat. No. 4,474,177 provides a method and apparatus for preparing the distal surface of a femur to receive a distal femoral prosthesis employing an intramedullary reamer which is used to internally locate the central long axis of the femur, an intramedullary alignment guide which is inserted into the space left in the intramedullary canal upon removal of the reamer and at least one femoral surface modifying instrument which cooperatively engages with a guide handle attached to the intramedullary alignment guide to accomplish the shaping of the distal femoral surface. The intramedullary alignment guide has a rod portion extending into the femoral intramedullary canal whose central long axis corresponds with the central long axis of the femur. The guide handle is attached to that rod portion at a preselected angle such that the shaping instruments fixed thereto assume the proper alignment with respect to the central long axis of the femur such that the distal femoral surface is shaped relative to that axis in a simple and accurate manner.

An improved triplanar knee resection system, disclosed in U.S. Pat. No. 4,487,203, provides a system for preparing a knee joint for a prosthesis. The apparatus of the triplanar knee system includes a single guide member for use in resecting the distal femoral condyles, the proximal tibia, and the distal femur. The guide member cooperates with a simplified set of instruments, including femur and tibia guide rods, a tibia adaptor, a tibia bar, and a femur bar, for establishing equal flexion and extension gaps and triplanar resections. The method of the triplanar knee system provides a simplified procedure for use by an orthopedic surgeon in properly preparing a knee joint for implantation of a prosthesis.

The Petersen U.S. Pat. No. 4,567,886 discloses a spacer guide for utilization in total knee surgery for establishing size of prosthesis and position of cuts for total knee replacement surgery includes a generally L-shaped base member for attachment to the anterior femoral cortex of a prepared femur with a generally L-shaped adjustable support member adjustably secured to the base support member and a vertically positionable indicator slide having a squaring jig for cooperative engagement and alignment with the cutting head of a tibia alignment and resection guide for squaring the tibia and femur and including indicator means for indicating the position of a tibia plateau cut and indicating the size and positioning for a distal femoral cut for indicating the sizing of the both the tibial and femoral prostheses.

The Kenna et al. U.S. Pat. No. 4,464,729 discloses a prosthetic knee implanted after cutting the femur and tibia with the aid of instruments which include axial alignment guides and a series of cutting jigs.

A method and apparatus for resecting a distal femoral surface is disclosed in U.S. Pat. No. 4,703,751 in which an intramedullary rod is inserted through the distal surface of the femur and along the femoral shaft access, leaving a protruding end; a jig is attached to the protruding end, the jig having a shaft for receiving the rod end and a support plate attached to an end of the shaft and extending parallel to the rod; attaching a reference bar to the shaft, the bar having a pair of opposing flanges and a central opening which receives the shaft therethrough, and adjusting the bar on the shaft such that the flanges contact condylar apeces of the femur; fixing the jig relative to the femur; attaching a cutting plate to the jig, the cutting plate having blade guides thereon, pivoting the cutting plate relative to the jig such that the blade guides made a predetermined angle with the rod, and securing the cutting plate to the jig; and inserting a saw blade through the blade guides to make a resection of the distal femoral surface. In the preferred embodiment, the shaft includes a plurality of bores along its length, each sized to receive the rod therethrough so that the distance between the rod and the support plate may be adjusted to accept different sized anterior femur portions. Also in the preferred embodiment, the apparatus includes a plurality of guide bars, each sized to space the blade guides a predetermined distance from the condylar apices.

The Kaufman et al. U.S. Pat. No. 4,721,104 relates to a surgical apparatus for providing an accurate recess in a distal femoral surface for the intercondylar stabilizing housing of a posterior-stabilized knee implant prosthesis which apparatus comprises a template having a bottom surface which is adapted to be placed in an aligning relationship with the flat surface of a distal femur which has been partially shaped to receive the femoral component of a posterior-stabilized knee implant prosthesis and a U-shaped slot passing through the template where the slot is of substantially the same size and shape as the outer periphery of the intercondylar stabilizing housing present on the femoral component to be implanted and a drilling means, preferably in the form of an endmill cutter, having a stop means thereon and the drilling means closely engages the sides of the U-shaped slot in the template so that the drilling means can be passed through the U-shaped slot until the stop means contacts a surface of the guide and is then drawn along the slot to create a precisely shaped and aligned recess in the femur for receipt of the intercondylar stabilizing housing. In a more preferred embodiment, the template is composed of a drilling means guide which fits over a femoral trial prosthesis which is used for trial reductions after the drill guide is used and removed.

The Russell et al. U.S. Pat. No. 4,722,330 relates to distal femoral surface shaping guide for mounting on a intramedullary alignment guide which references the central long axis of the femur in shaping the distal femoral surface and a method for shaping the distal femur using the shaping guide. The alignment guide of the present invention is adjustable relative to the surface of the anterior femoral cortex to insure that the anterior aspect of the distal femoral condyles is resected relative to that surface and, preferably, at the same level as that surface. The alignment guide of the present invention provides a main body which remains attached to the intramedullary alignment guide throughout the entire shaping of the distal femur. It thus requires fewer cutting guides and alignment steps than other shaping guides while allowing greater accuracy in shaping the distal femur relative to the central long axis of the femur.

An improved tibial cutting jig is disclosed in U.S. Pat. No. 4,736,737, provided for use in obtaining accurate tibial resection in the course of a total knee prosthesis implantation procedure. The tibial cutting jig includes a base for sliding reception onto an intramedullary alignment rod pre-installed generally along the longitudinal axis of the tibia. The base includes laterally extending outriggers carrying removable measurement keys of selected size for spacing the base above the tibial plateau by a selected dimension. An anterior saw guide depends from the base and is thus positioned relative to the tibial plateau in accordance with the sizes of the measurement keys.

The Buechel et al. U.S. Pat. No. 4,738,253 discloses a guide for a cutting device used to make a surgical cut in a first bone in desired spatial relationship with a pre-existing cut in a second bone is disclosed to include a means for contacting the pre-existing cut to establish a reference for the desired spatial relationship and a body member engaging the means for contacting and including a guide surface for establishing the desired spatial relationship and guiding a surgical cutting tool to cut the first bone in a plane which is not normally inclined with respect to the long axis of the first bone.

Another Buechel et al. U.S. Pat. No. 4,738,254 discloses a positioner for positioning a surgical instrument which acts as a guide for a cutting instrument which produces a surgical cut in an anatomical structure; in one embodiment the positioner positions a surgical instrument which acts as a guide for the cutting instrument at a predetermined position with respect to a previously resected surface whereby a further resection is made at a predetermined position with respect to the previously resected surface; and in a further embodiment the positioner acts as a adaptor for a surgical instrument which aids in producing surgical sections thereby allowing the surgical instrument to produce surgical cuts at various predetermined positions relative to a previous surgical cut made at one of several levels.

The Dunn et al. U.S. Pat. No. 4,759,350 provides a system of instruments for shaping the distal femur and proximal tibia surfaces to receive components of a knee prosthesis for knee replacement surgery. The system references the femur intramedullary channel with a femoral alignment guide to prepare the distal femur that, in turn, is a reference for several cutting guides for sequential attachment to the femoral alignment guide and prepared bone surfaces whereby the prepared distal femur is prepared to a flat surface that is perpendicular to the patients mechanical axis with bone surfaces adjacent thereto sectioned to surfaces that are at right angles to that distal femur surface with chamfers therebetween to receive the femur component of a knee prosthesis. A tibial cutting guide is provided for preparing the proximal tibia that consists of a sleeve, with a tube telescoped therein, the ends thereof including pin arrangements for connecting them into the tibia, between the ankle and near the proximal tibia, an open tube end of the tibial cutting guide to receive a rod telescoped therein that mounts a cutting guide platform and includes a screw arrangement for releasably maintaining the road and tube together. The cutting guide platform includes a body with a saw guide slot formed therethrough to receive a saw blade to cut across the proximal tibia to form a surface for accommodating a tibial component of the knee prosthesis, the cutting guide platform body further including an arrangement for securing it to the tibia, slightly below the proximal tibia, and a tibial resection guide for setting a depth of cut across the proximal tibia.

U.S. Pat. No. 4,773,407 issued to Petersen discloses a method and instruments for resection of the distal femur. The instruments include a distal femoral resector and a femoral alignment guide/rod. The distal femoral resector is designed to be attached to the distal femur on a plane filed on the anterior femoral cortex. The distal femoral resector includes a feeler gauge laterally adjustable to adapt to the intercondylar notch of the particular patient and further includes a rotating rod having openings therethrough for fastening pins, which rotating rod is designed to facilitate the placement of the resector on the anterior femoral cortex in a flush manner. The femoral alignment guide/rod includes a plate insertable within a slot in the resector designed for the insertion of the cutting tool and further includes a pivotable rod which may be utilized to align the resector with the mechanical axis of the leg. The rod may then be pivoted to a position facilitating the insertion of a fastening pin through the resector. The method of operation using these instruments is also disclosed.

U.S. Pat. No. 4,892,093 issued to Zarnowski et al. discloses a cutting guide for guiding a saw blade during the preparation of a femur for the implant of the femoral component of a knee prosthesis includes guide surfaces for enabling the cutting of all four of the anterior femoral cut, the posterior femoral cut, the anterior chamfer and the posterior chamfer, fully and completely, with certitude and accuracy, while the cutting guide remains located and secured to the femur in a single position on a transverse surface located along the distal femur.

The Dale et al. U.S. Pat. No. 4,893,619 discloses a device for guiding an osteotomy to be performed on the proximal end of a humerus that has a proximal saw guide alignable on a selected surface of the proximal end of the humerus for defining a saw line thereon; a radial arm connecting the saw guide to a distal mechanism for stably aligning the saw guide, the distal alignment mechanism has a pair of opposing lateral and medial epicondyle arms pivotally engagable with the lateral and medial sides of the distal end of the humerus, the epicondyle arms being pivotally mounted in a distal cross arm, the distal end of the radial arm being slidably mounted in the cross arm for distal to proximal slidable movement therein; the proximal end of the radial arm being rotatably connected to the saw guide through a proximal guide bar; the radial arm being supported above the humerus by the proximal guide bar and the epicondyle arms.

U.S. Pat. No. 4,907,578 relates to an improved method and instruments for a resection of the distal femur. The parent application discloses a femoral alignment guide/rod including a plate insertable within a guide slot in the resector which is also used for the guided insertion of a cutting tool. The present invention improves upon this structure by providing an auxiliary attachment member on the resector allowing attachment of a new femoral alignment guide/rod on the resector housing proximal to the cutting tool guide slot, which new guide/rod allows easier access to various resector components. In a further aspect, structure is provided allowing the use of the resector with an intramedullary rod to increase accuracy. In this aspect, a gauge is incorporated in the resector which allows compensation for the angle between the mechanical axis of the leg and the longitudinal extent of the internal cavity of the femur while also allowing compensation or correction for specific anatomical conditions such as, for example, valgus correction.

The Whiteside et al. U.S. Pat. No. 4,935,023 relates to a distal femoral surface shaping guide for mounting on an intramedullary alignment which references the central long axis of the femur in shaping the distal femoral surface and a method for shaping the distal femur using that shaping guide with particular applicability for shaping one condyle for attachment of a unicondylar prosthesis. The alignment guide of the present invention is adjustable relative to the surface of the condyle to insure that the distal femoral condyle is resected relative to that surface. The alignment guide of the present invention utilized visual sighting studs and provides a main body which remains attached to the intramedullary alignment guide throughout the entire shaping of the distal femur.

The Bowman et al. U.S. Pat. No. 4,952,213 discloses an apparatus for placing a bone cutting saw cutting guide adjacent a proximal surface of a human tibia bone having an elongated rod inserted into the tibia for clampingly supporting a rotating bar on the central longitudinal axis of the tibia bone. The bar being extended from the rod and connected to a pivot device which in turn is connected to a support arm that holds a saw cutting guide against a proximal portion of the tibia bone. The rotation angle of the rod determining the medial-lateral inclination of the saw cutting guide and the pivot device determining the anterior-posterior inclination of the saw cutting guide. The support arm is adjustable in length to determine the height of the saw cutting guide.

The Dunn et al. U.S. Pat. No. 4,959,066 provides an osteotomy guide assembly for femoral neck osteotomy and includes a saddle locator assembly and a saw guide attachment. The saddle locator assembly includes a barrel-shaped locating device that locates the saddle region of the proximal femur. The barrel further includes a transverse support bar extending from the barrel. The barrel is positioned over an intramedullary shaft which is temporarily positioned in and extends from the medullary canal of the femur. A saw guide is used in conjunction with a saddle locator assembly. The saw guide is attached to the support bar by a single locking means which provides for positional adjustment of the saw guide relative tot he support bar in two directions, including adjustment in the anterior-posterior direction along the transverse support bar and axially along the femur via a post which extends from the saw guide.

The Whiteside et al. U.S. Pat. No. 5,002,545 provides a shaping guide to permit accurate shaping of the tibial plateau while saving the anterior cruciate ligament. An alignment rod is located anterior to the anterior cruciate ligament and along the anterior cortex of the intramedullary canal of the tibia provides points of reference for all shaping operations. The shaping guide of the present invention is adjustable with respect to the handle portion of the rod so that the amount of resection of the tibial plateau can be controlled readily by the surgeon by raising or lowering of the cutting guide surfaces for resection of the tibia.

The Mikhail et al. U.S. Pat. No. 5,108,405 discloses a system for performing hip prosthesis revision surgery includes a trial femoral component having a passageway which, upon insertion in the cavity left after removal of the original prosthesis, provides guide means for drilling a channel to receive a guide wire which, upon removal of the trial femoral component, serves as guide means for progressively larger reamers.

SUMMARY OF THE INVENTION

The present invention provides an improvement over prior art cutting guide systems for preparing a patient s distal femur to receive a distal femoral prosthesis component.

The apparatus of the present invention includes a cutting guide body that can be moved in an anterior and posterior direction relative to a valgus module.

The valgus module has an anchoring mechanism that rides with the module. The anchoring mechanism can be quickly tightened by the surgeon in a desired position after the module has been moved in an anterior posterior direction. Tightening occurs before the cutting block is even affixed to the patient s distal femur. The cutting block can be exactly positioned by the surgeon to fit a particular anatomical situation with a particular patient. Further, a plurality of the valgus modules can be provided, interchangeable for different valgus angles as selected by the surgeon.

The surgeon can pick one valgus module, very quickly position the module and cutting block in a desired location, and then replace the module with a different module if the fit is not a good one according to the surgeon.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 12 is an partial perspective exploded view of the valgus module portion of the preferred embodiment of the apparatus of the present invention;

FIG. 13 is a fragmentary view of the sleeve component of the valgus module portion of the preferred embodiment of the apparatus of the present invention;

FIG. 14 is an end fragmentary view of the valgus sleeve component of the module portion of the preferred embodiment of the apparatus of the present invention;

FIG. 15 is a side fragmentary view of the sleeve component of the valgus module portion of the preferred embodiment of the apparatus of the present invention;

FIG. 16 is a side fragmentary view of the posterior referencing paddles of the preferred embodiment of the apparatus of the present invention;

FIG. 17 is a front view of the posterior referencing paddles of the preferred embodiment of the apparatus of the present invention;

FIG. 18 is a rear view of the posterior referencing paddles of the preferred embodiment of the apparatus of the present invention;

FIG. 19 is a bottom fragmentary view illustrating the posterior referencing paddles of the preferred embodiment of the apparatus of the present invention;

FIG. 20 is fragmentary perspective view illustrating the posterior referencing paddles of the preferred embodiment of the apparatus of the present invention;

FIG. 21 is a top view illustrating the posterior referencing paddles of the preferred embodiment of the apparatus of the present invention;

FIGS. 27-28 are perspective views schematically illustrating the placement of cuts on the patient s distal femur as part of the method and apparatus of the present invention;

FIGS. 29-30 are perspective views of the patient s distal femur showing placement of the femoral prostheses trials thereon;

FIG. 31 is a perspective view of the preferred embodiment of the apparatus of the present invention illustrating a posterior referencing technique;

DETAILED DESCRIPTION OF THE PREFERRED EMBODIMENT

Figure 1:
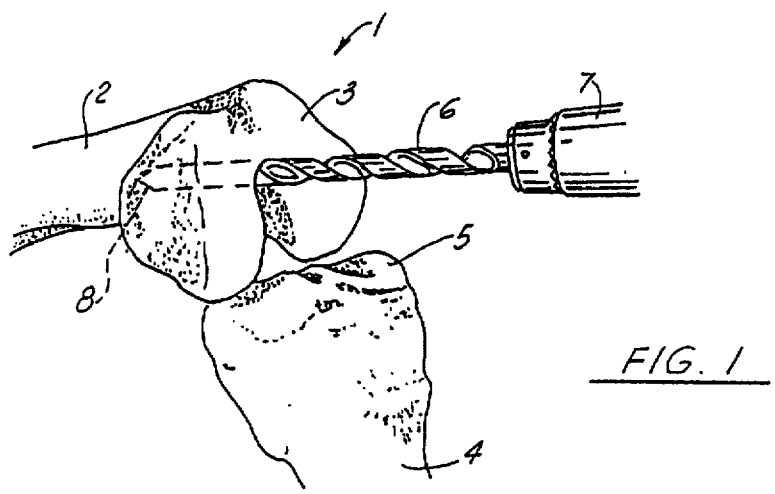
FIG. 1 is a perspective view illustrating the femoral preparation method step of the present invention.

FIG. 1 illustrates femoral preparation as the first part of the method of the present invention. The patient s knee joint 1 is flexed and positioned for surgery. The femur 2 and distal femur 3 are shown above the patient s tibia 4 and proximal tibia 5. Once the knee joint 1 is flexed as shown in FIG. 1, the femoral intramedullary canal 8 is drilled to accept an intramedullary reamer rod 35. The reamer rod 35 (for example eight millimeter diameter) is slowly inserted into the patient s femoral shaft or intramedullary canal 8.

Figure 2:
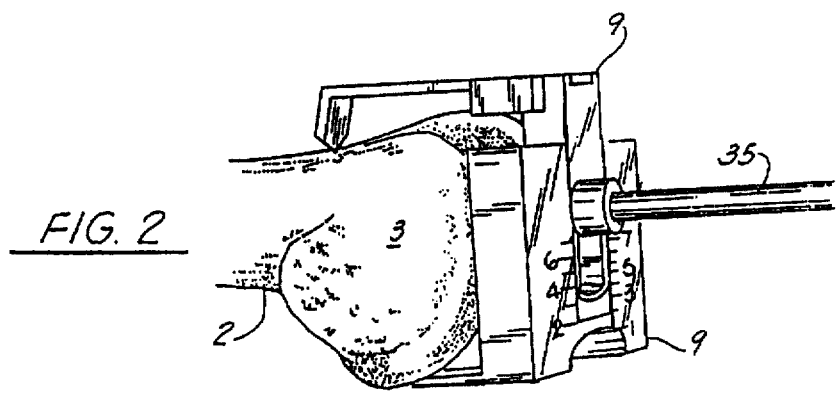
FIG. 2 is a perspective view illustrating another method step of the present invention, namely a sizing of the femur.

In FIG. 2, the patient s femur is sized with a femoral sizer 9. A femoral sizer 9 is placed on the patient s distal femur 3 and over the reamer rod 35. Femoral sizers are commercially available and known in the art. The proper size prosthesis is determined by reading a scale on the femoral sizers. The femoral sizer 9 is removed leaving the reamer rod 35 in place within the patient s femoral intramedullary canal 8.

Figure 3A:
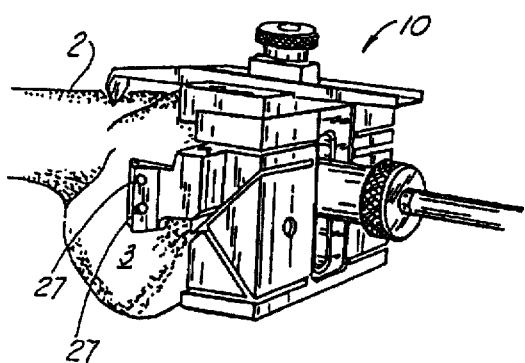
FIGS. 3A-3B are perspective views illustrating additional method steps of the present invention, namely placement of the femoral cutting block.
Figure 4:
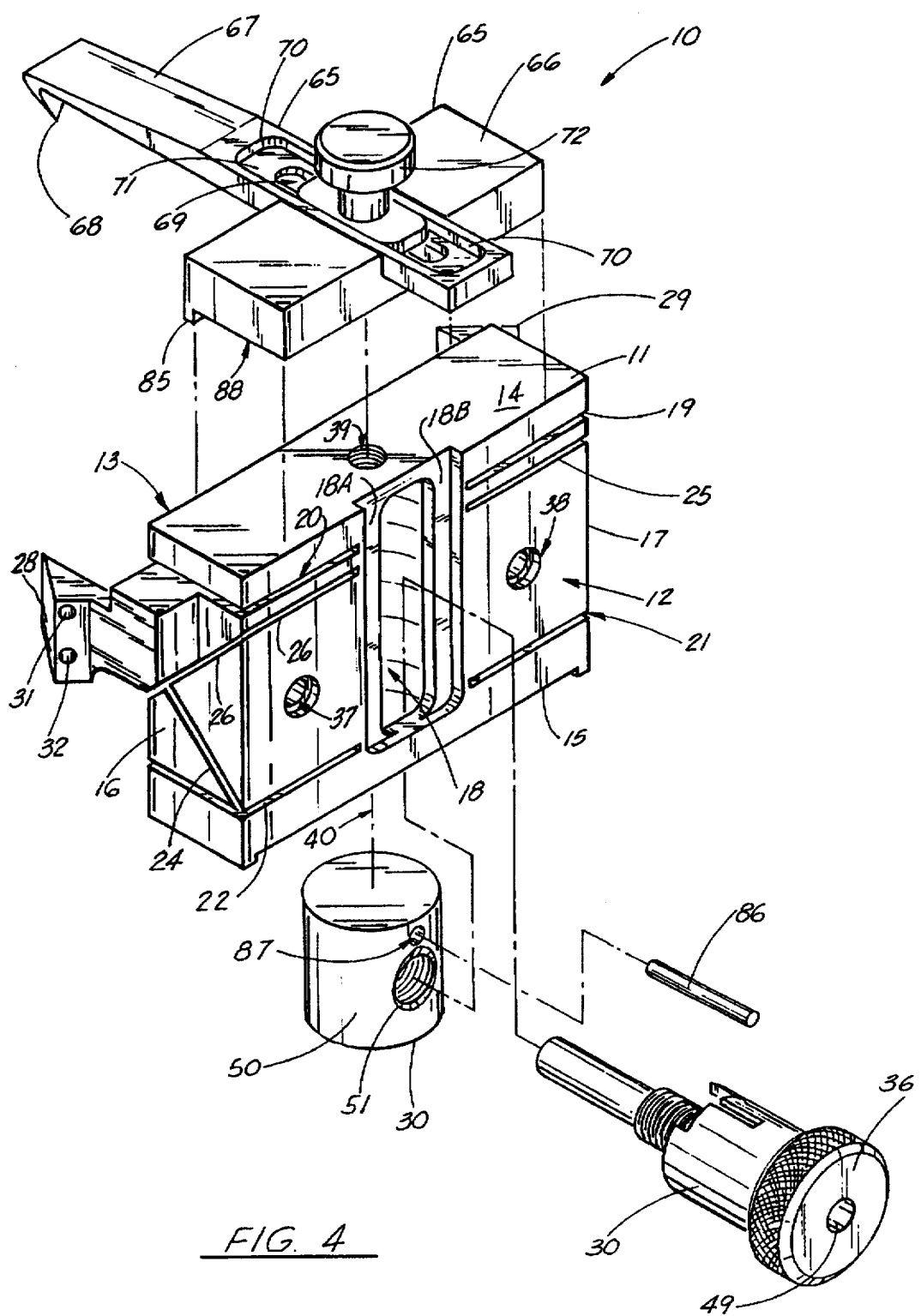
FIG. 4 is a perspective exploded view of the preferred embodiment of the apparatus of the present invention.
Figure 5:
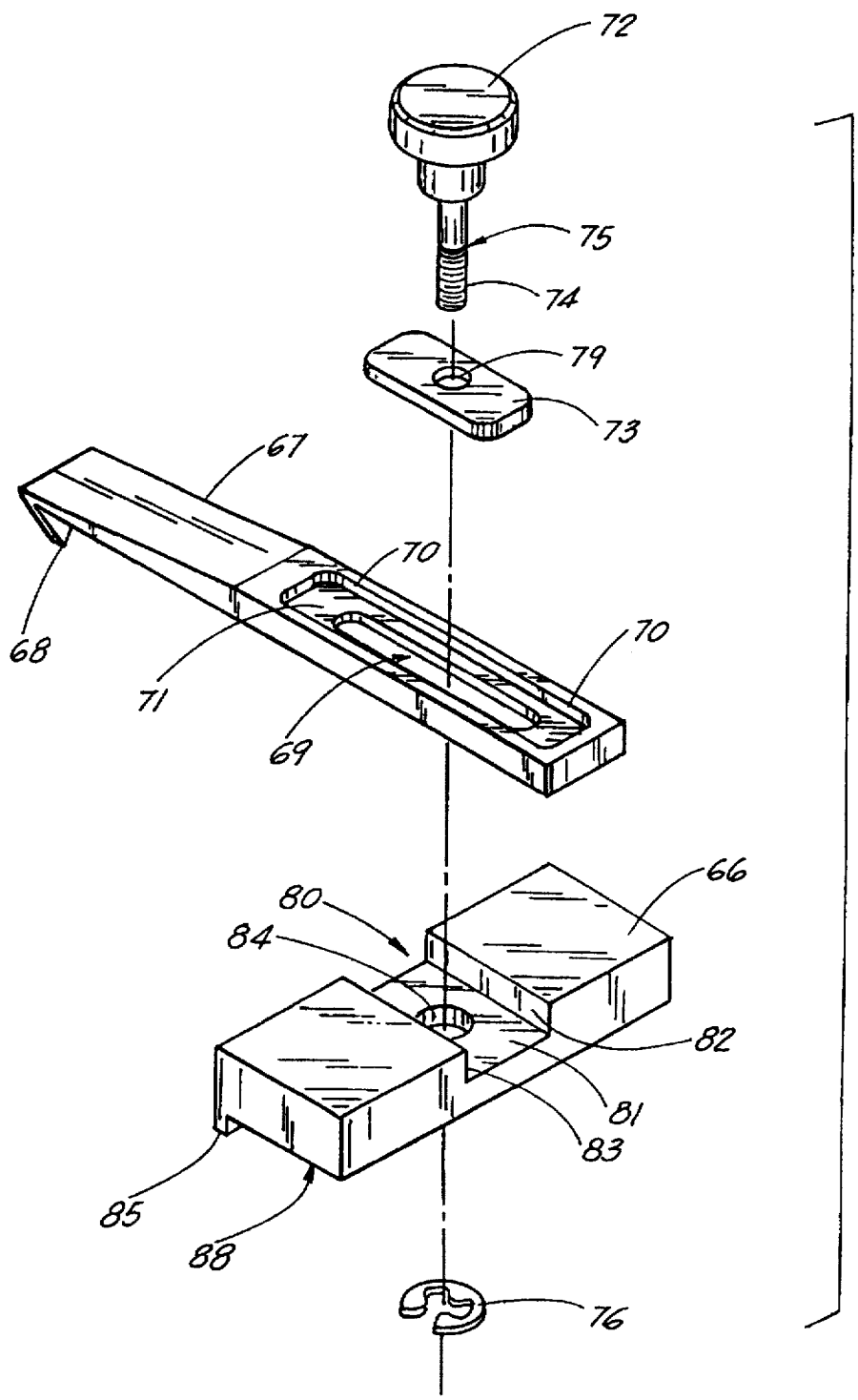
FIG. 5 is a partial perspective exploded view of the preferred embodiment of the apparatus of the present invention.
Figure 6:
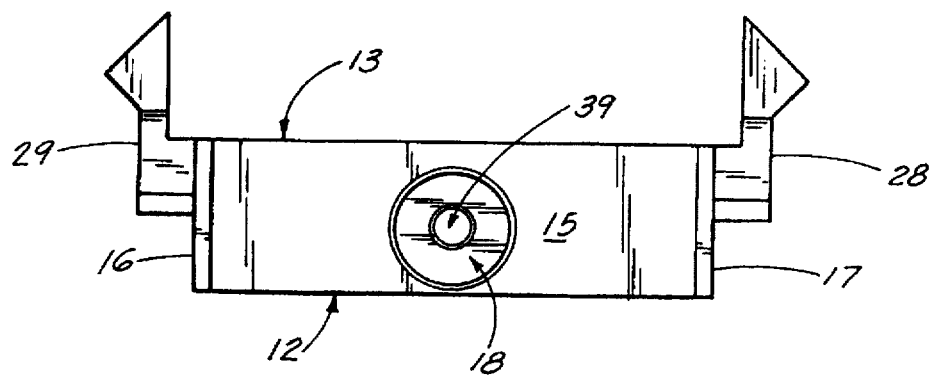
FIG. 6 is a partial end view of the preferred embodiment of the apparatus of the present invention.
Figure 7:
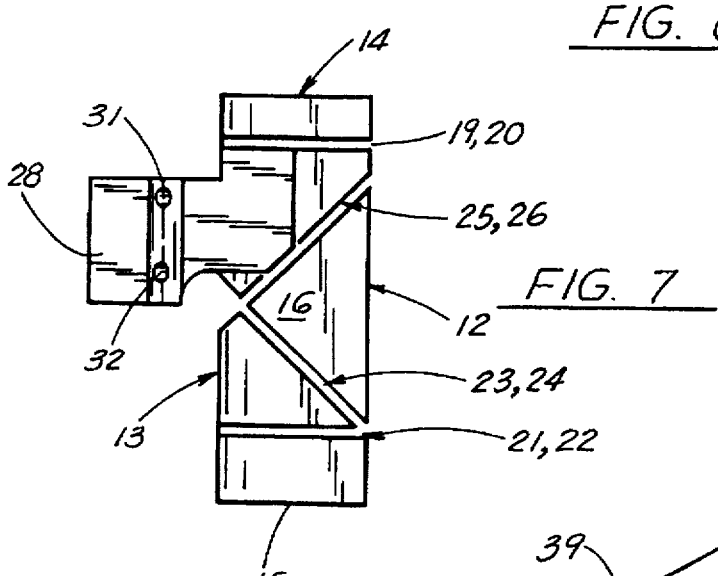
FIG. 7 is a partial side view of the preferred embodiment of the apparatus of the present invention.
Figure 8:
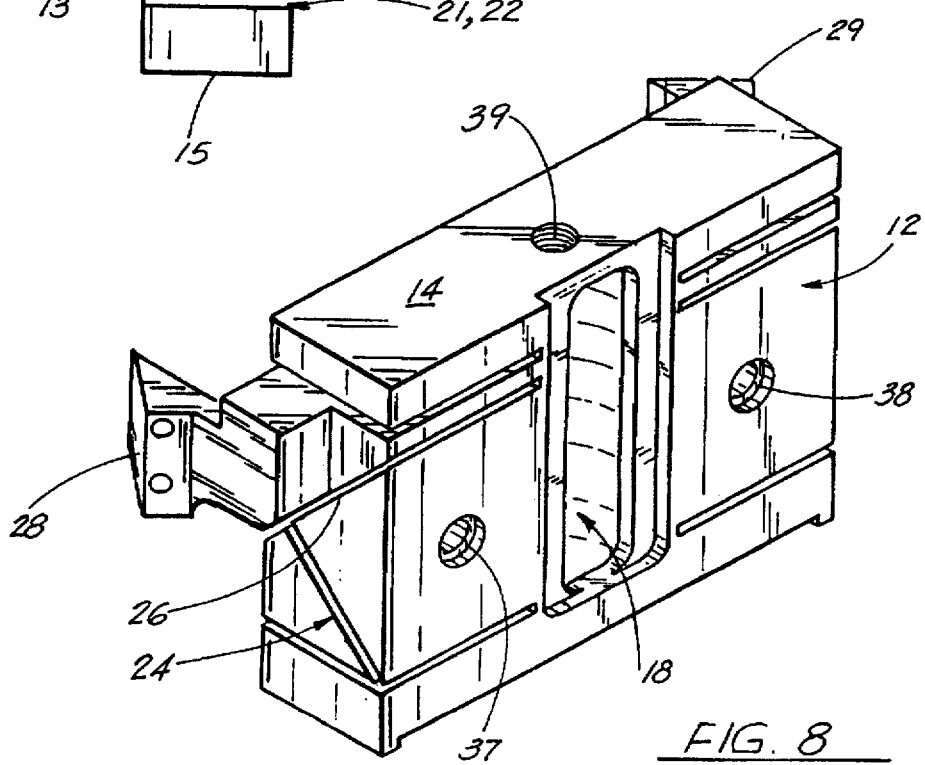
FIG. 8 is a partial perspective view of the preferred embodiment of the apparatus of the present invention.
Figure 9:
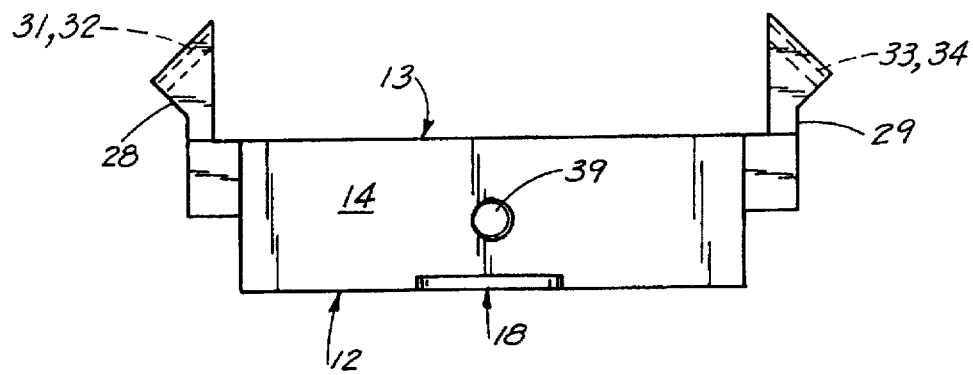
FIG. 9 is a partial end view of the preferred embodiment of the apparatus of the present invention.
Figure 10:
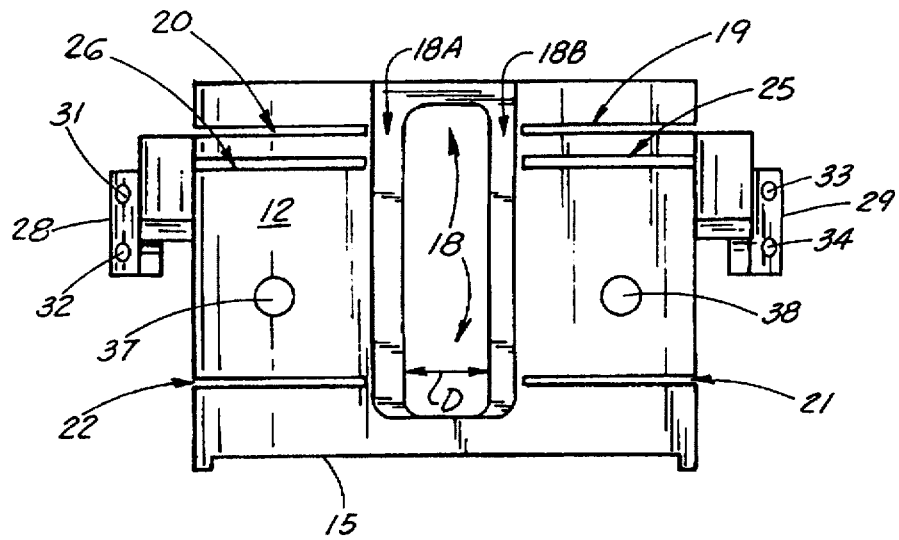
FIG. 10 is a partial top view of the preferred embodiment of the apparatus of the present invention.
Figure 11:
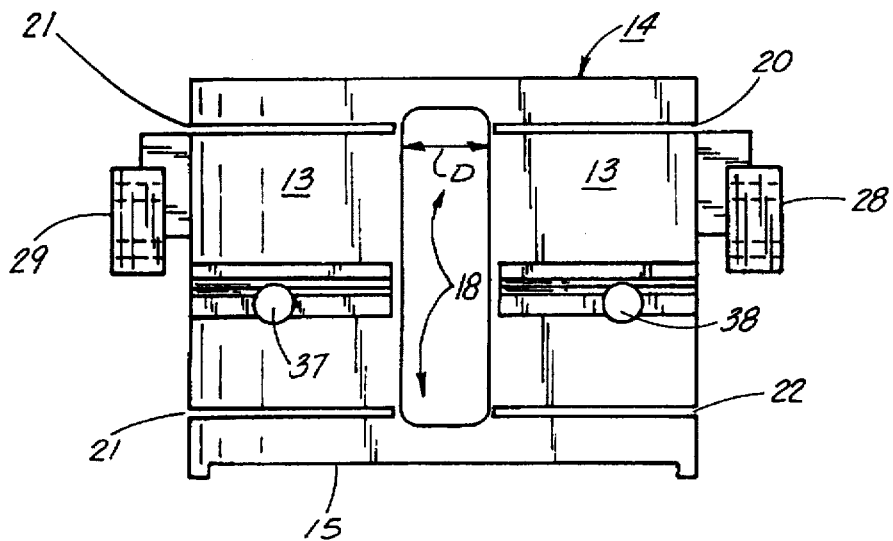
FIG. 11 is partial bottom view of the preferred embodiment of the apparatus of the present invention.
Figure 22:
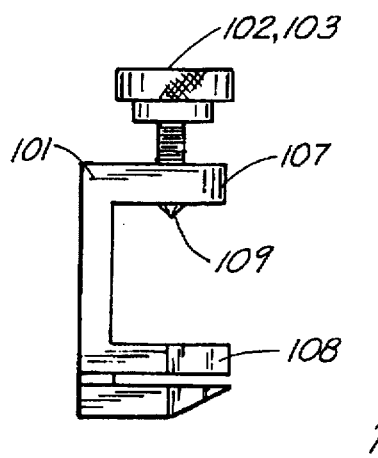
FIG. 22 is a side fragmentary view of the distal cutting block portion of the preferred embodiment of the apparatus of the present invention.
Figure 23:
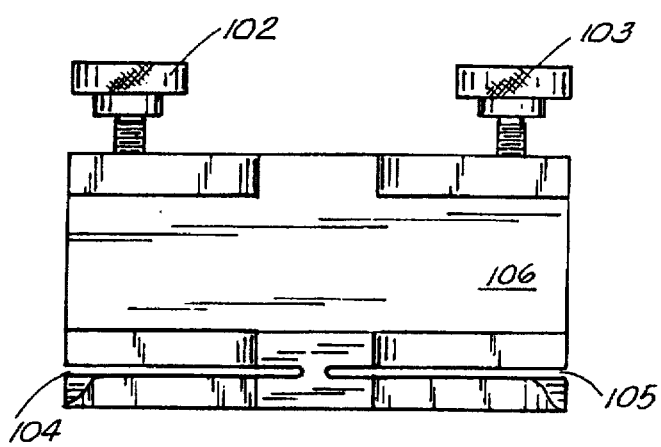
FIG. 23 is a bottom view of the distal cutting block portion of the preferred embodiment of the apparatus of the present invention.
Figure 25:
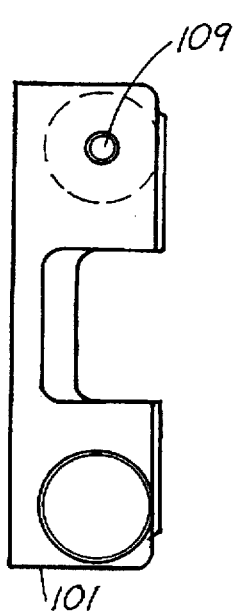
FIG. 25 is another end fragmentary view of the distal cutting block of the preferred embodiment of the apparatus of the present invention.
Figure 24:
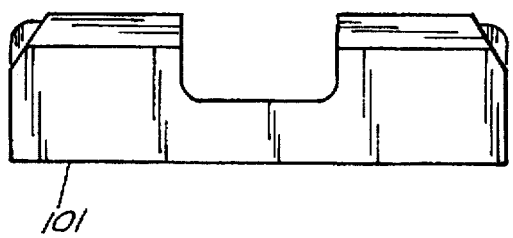
FIG. 24 is an end fragmentary view of the distal cutting block of the preferred embodiment of the apparatus of the present invention.
Figure 26:
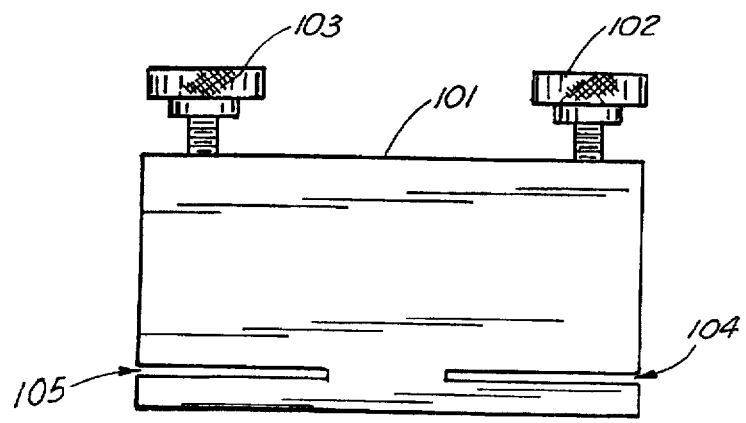
FIG. 26 is a top fragmentary view illustrating the distal cutting block portion of the preferred embodiment of the apparatus of the present invention.

The apparatus 10 of the present invention can be selectively used with either anterior or posterior referencing. If the surgeon wishes to use an anterior referencing technique, the feeler gauge 65 of FIGS. 3A, 4, and 5 is used. FIG. 3A shows anterior referencing. During anterior referencing, feeler gauge 65 (and not the posterior referencing paddle 90) is affixed to block 11. During posterior referencing, the posterior referencing paddle 90 of FIGS. 16–21 and 31 (and not feeler gauge 65) is affixed to cutting block 11.

With anterior referencing the pointer 68 of feeler gauge 65 is placed against the patient s anterior cortex, then the valgus module 30 tightened. With anterior referencing, the paddle 90 is affixed to block 11, the paddle flanges 91, 92 placed against the patient s posterior condylar surfaces and then the valgus module 30 is tightened.

Figure 3B:
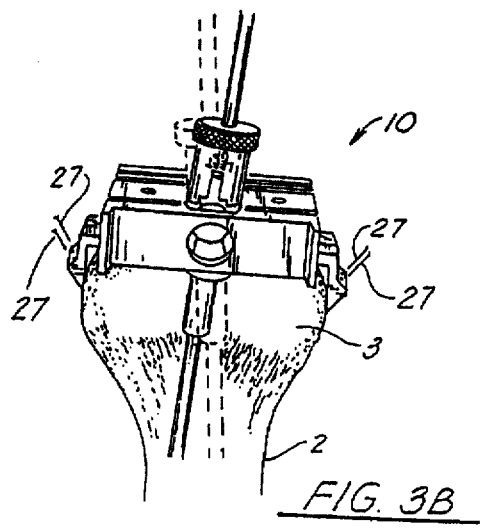

In FIGS. 3 and 3A, the femoral cutting block is designated generally by the numeral 10. FIGS. 4–21 illustrate with more detail the preferred embodiment of the apparatus of the present invention designated in FIG. 4 generally by the numeral 10. Femoral cutting instrument 10 includes a cutting block 11 body having an upper planar surface 12 and a lower planar surface 13. Cutting block 11 also provides an anterior surface 14 and a posterior surface 15. Cutting block body 11 includes side walls 16, 17.

An internal, anterior posterior (A/P) slot 18 extends between anterior surface 14 and posterior surface 15. In the preferred embodiment, the slot 18 does not completely, extend to surfaces 14, 15. Slot 18 accepts valgus module 30 during use. Valgus module 30 has a cylindrical member 50 that slides in slot 18, being movable along a path (axis 40) that extends generally between surfaces 14, 15 and parallel to sides 16, 17. The slot 18 has curved sidewalls 18C that fit closely to the curved contour of cylindrical member 50. Further, the slot 18 has a thickness D at surfaces 18A, 18B and at surface 13 that is smaller than the diameter of cylindrical member 50. Therefor, member 50 can only be removed from slot 18 at the open end of slot 18 (see FIG. 6) at surface 15. Thus, when knob 36 is tightened, cylindrical member 50 bears against the curved sidewalls 18C of slot 18. Appendages 61, 63 of sleeve 55 bear against the flat surfaces 18A, 18B adjacent slot 18. Threads 47 of hollow sleeve member 46 engage internally threaded bore 51 of cylindrical member 50. This combined action tightly affixes valgus module 30 to block 11. Because appendages 61, 63 are of different length, bore 49 (and reamer 35) are angled relative to block surfaces 12, 13.

The valgus module 30 can be adjusted into several positions relative to the block 11 by sliding the module to the desired location on the block 11. Module 30 provides this adjustability relative to block 11 when the module 30 is referenced upon an intramedullary rod or reamer 35, and prior to attachment of cutting block body 11 to the patient s distal femur 3. Block 11 is affixed to reamer 35 by placing the rod through open ended bore 49 of valgus module 30.

Once the surgeon has selected the desired location of cutting block 11 using valgus module 30 and intramedullary rod 35, all adjustments are complete. The cutting block 11 can then be firmly affixed to the patient s distal femur using bone spikes 27. A bone spike 27 can be placed through either of the spike supports 28, 29 each spike support 28, 29 providing openings 31–34, as shown in the drawings.

Once positioned in a desired location relative to the patient s distal femur 3, the surgeon can rigidly lock the valgus module 30 to cutting block 11 by tightening knurled knob 36. The surgeon can then make a number of cuts in the patient s distal femur 3 as part of the surgical procedure of implanting a knee prosthesis.

Cutting block 11 provides a pair of anterior cutting guide slots 19, 20 on opposite sides of anterior-posterior slot 18. Slots 19, 20 are parallel to surface 14 and form a right (90°) angle with axis 40 of slot 18. Cutting block 11 provides a pair of posterior cutting guide slots 21, 22 on opposite sides of anterior-posterior slot 18. Slots 19, 20 are parallel to slots 19, 20 and to surface 14. Cutting block 11 provides a pair of co-planar anterior chamfer cutting guide slots 23, 24 and a pair of co-planar posterior chamfer cutting guide slots 25, 26.

Figure 32:
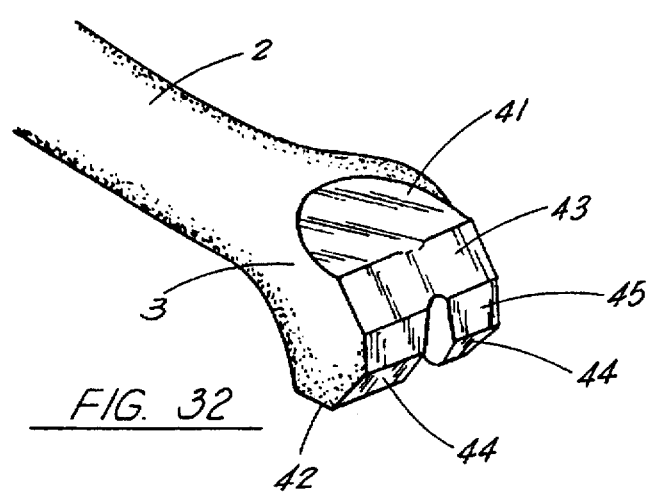
FIG. 32 is a perspective view illustrating the patient s femur after surgical cuts have been made including anterior, posterior, distal and chamfer cuts.
Figure 33:
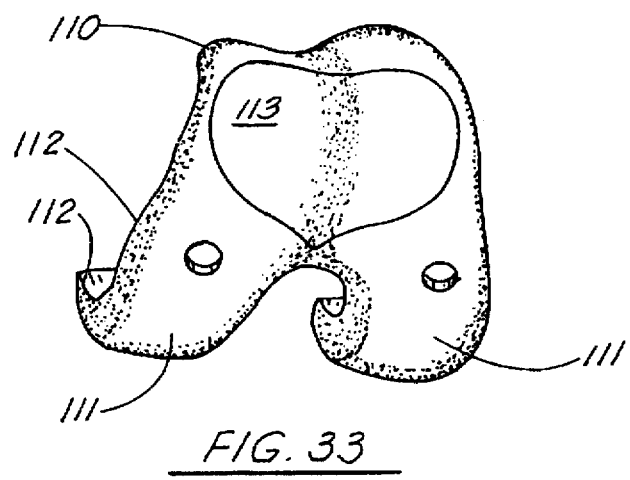
FIGS. 33-34 are perspective views of the femoral prosthesis trial portion of the preferred embodiment of the apparatus of the present invention.
Figure 34:
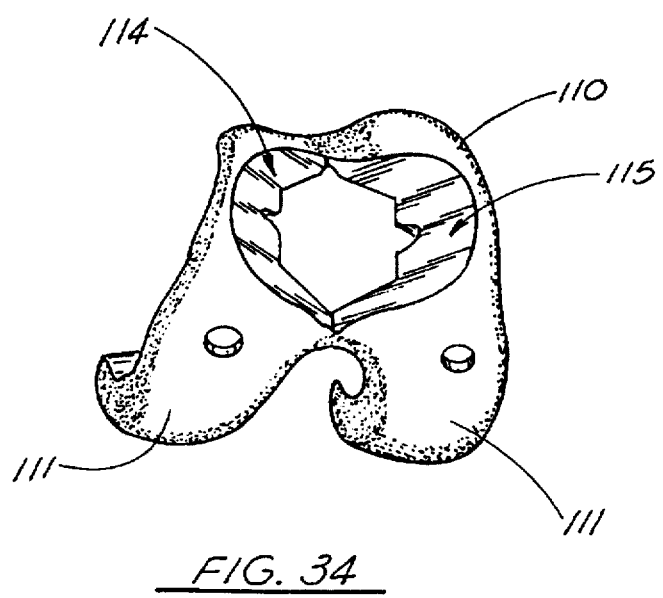

The aforementioned cutting guide slots 19–26 allow the surgeon to make anterior and posterior cuts, and chamfer cuts for receiving a femoral prosthesis. These cuts shape the patient s distal femur 3 to receive a femoral prosthesis. In FIG. 32, the aforedescribed cuts have been formed by the surgeon including anterior cut 41, posterior cut 42, anterior chamfer cut 43, and posterior chamfer cut 44, and distal cut 45. This distal cut 45 is made using a distal cutting block (FIGS. 22–26) as will be described hereinafter.

Block 11 has openings 37, 38 that receive pegs of a posterior referencing paddle 90 (FIGS. 16–21) if posterior referencing is selected by the surgeon. An internally threaded opening 39 in block 11 anterior surface 14 receives a threaded portion 74 of feeler gauge 65 if anterior referencing is selected.

FIGS. 4 and 5 illustrate the feeler gauge 65 portion of the preferred embodiment of the apparatus of the present invention 10. The feeler gauge 65 is used with an anterior referencing technique because the surgeon uses the feeler gauge 65 to reference the patient s anterior cortical bone tissue. This is done by first affixing the cutting block 11 in a desired position on the patient s distal femur 3, mounting the cutting block 11 on reamer 35. The knob 36 is loosened. The bolt 72 is also loosened. Once the surgeon picks the proper location for the pointer arm 67 of feeler gauge 65, the feeler gauge 68 is then tightened by tightening the nut 72 against the threaded member 74. Now the proper location of block 11 has been determined and the valgus module 30 is tightened using knob 36. Upon tightening, the valgus module 30 forms an acute angle between the central longitudinal axis of reamer 35 and the parallel, opposed flat surfaces 12, 13 of block 11. The block 11 peripheral sides 14–18 are at right angles to each adjoining side and are also at right angles to the parallel flat surfaces 12, 13.

The feeler gauge 65 includes a support block 66 that receives pointer arm 67. Pointer arm 67 includes a pointer 68 that contacts that patient s anterior cortical bone tissue during anterior referencing. A longitudinal slot 69 in pointer arm 67 allows bolt 72 to pass therethrough and form a connection with internally threaded opening 39. A peripheral shoulder 70 surrounds longitudinal slot 69. Further, a flat surface 71 extends between longitudinal slot 69 and peripheral shoulder 70. The area of flat surface 71 and peripheral shoulder 70 receive plate 73 having an opening 79 therethrough. The plate 79 provides a bearing member for interfacing between bolt 72 and pointer arm 67. The bolt 72 is threadably engaged in threaded opening 39 of block 11.

Retaining ring 76 insures that all pieces of 65 do not come apart once assembled. Bolt 72 extends through opening 84 of support block 66, longitudinal slot 69 of arm 67, and opening 79 of plate 73. When the user tightens the nut 72, the plate 73 bears against the surface 71 of arm 67 and locks the arm 67 against support block 66.

Support block 66 includes a rectangular slot 80 that is configured to receive arm 67. Block 66 includes flat surface 81 and flat side walls 82, 83 that cradle arm 67. A transverse shoulder 85 extends along the flat under side 88 of support block 66. Upon assembly of feeler gauge 65 to block 11, the transverse shoulder 85 aligns with and fits the intersection of block 11 surfaces 13, 14.

FIGS. 4 and 12-15 show the valgus module 30 in more detail. The module 30 is comprised of a cylindrically shaped member 46 that includes smooth cylindrical unthreaded sections 48 and a cylindrical externally threaded section 47. The smooth sections 48 are included on opposite sides of threaded section 47.

The valgus module 30 includes a bushing or sleeve 55, a washer 54, a hollow sleeve 46, and a cylindrically-shaped member 50 (see FIG. 4). The hollow sleeve 46 includes a pair of spaced apart unthreaded sections 48 of small diameter with an externally threaded section 47 therebetween. Annular groove 52 is positioned at smooth section 48 between knob 36 and threaded section 47. The annular groove accepts lock ring 53. The hollow sleeve 46 extends through washer 54 and through the opening 58 of bushing 55. Bushing 55 has an open cylindrically-shaped center portion 56. One end of the bushing 55 is provided with an annular shoulder 57 so that opening 58 is smaller than the opened cylindrically-shaped center 56. A pair of appendages 61, 63 are provided at the end portion of bushing opposite annular shoulder 57. The appendages 61, 63 each provide a lower flat foot 62, 64. These flat surfaces 62, 64 bear against the flat surfaces 18A, 18B that extend longitudinally on each side of slot 18. In FIG. 15, it should be noted that the appendage 61 is longer than the appendage 63 and the surfaces 62, 64 are angled (as shown in FIG. 15) with respect to flat annular shoulder 57 and bore 49. This produces an angulation when the surfaces 62, 64 rest against the surfaces 18A, 18B. This produces a correction for the valgus angle as the intramedullary rod 35 mounted in opening 36 of hollow sleeve 46 forms an angle with the parallel flat surfaces 12, 13 of cutting block 11. Further, it should be understood that the apparatus 10 of the present invention is reversible for the left/right leg of the patient. The surgeon can simply rotate the bushing 55 so that the longer appendage 62 bears against the selected surface 18A or 18B depending upon which knee of the patient is being implanted with a knee prosthesis.

A pair of slots 59, 60 in bushing 55 accept lock pin 86 that is implanted in opening 87 of cylindrical member 50. The combination of lock pin 86 and the slots 59, 60 prevent rotation of bushing 55 relative to block 11 during use.

FIGS. 16-21 show a posterior paddle 90 that can be used for posterior referencing. Paddle 90 includes a pair of spaced apart flanges 91, 92 that engage the posterior condyles of the patient's femur during referencing. There can be a space 93 between the flanges 91, 92. A pair of spaced apart pegs 94, 95 fit the corresponding openings 37, 38 in cutting block 11. It should be understood that when the paddle assembly is used in combination with block 11, the anterior referencing feeler gauge 65 is not used. This allows the surgeon if so desired to use a posterior referencing technique. A base member 96 extends between the flanges 91, 92 and the posts 94, 95. The base 96 provides a flat surface 97 that registers tightly against flat surface 12 of cutting block 11. The base 96 can include a pair of appendages 98, 99 with a space 100 therebetween.

FIGS. 22-26 show a distal cutting block 101 that is used for cutting the patient's distal femur after the anterior and posterior cuts 41, 42 have been made and after the anterior and posterior chamfer cuts 43, 44 have been made using block 11. After the block 11 is affixed to the patient's distal femur 3, the distal block 101 is affixed using set screws 102, 103 to cutting block 11, and more particularly to the anterior 14 surface thereof, as shown in FIG. 28.

The block 101 provides a pair of spaced apart slots 104, 105 that is used to guide a cutting instrument C during a cutting of the distal femur as shown in FIG. 28. The block 101 provides a flat surface 106 that fits closely against the anterior surface 14 of cutting block 11. A pair of spaced apart flanges 107, 108 register respectively against the surfaces 13 and 12.

Each of the set screws can have a conically-shaped end portion 109 that can fit in a groove defined by the chamfer cuts 25, 26 at surface 12 at block 11. The surgeon simply mounts the cutting block 101 on the anterior 14 surface of block 11 and tightens the set screws 102, 103 and until the conical portion 109 engages surface 12 of block 11. This forces the flange 108 into tight engagement with the flat surface 13 of cutting block 11. Upon assembly, the slots 104, 105 are spaced away from surface 13 so that the surgeon can pass the cutting saw C through the slots 104, 105 and to cut the distal femur as shown in FIG. 28.

FIGS. 33, 34 and 29-30 illustrate the use of a trial prosthesis designated generally by the numeral 110. The trial prosthesis 110 has a generally J-shaped articulating surface 111 and a non-articulating surface 112 that has five surfaces that correspond to the cuts 41-45 made on the patient's distal femur as shown in FIG. 32.

An insert 113 is removably mounted to the center of trial prosthesis 110. A pair of flat cutting guide surfaces 114, 115 are exposed. The surfaces 114, 115 intersect each other to form an angle of between 0 and 180 degrees.

The surgeon can then use a cutting instrument C resect the patello femoral groove by forming two (2) cuts, registering flat blade B against cutting guide surfaces 114, 115 as shown in FIG. 29. The resulting V shaped notch 116 accommodates a projection on the posterior surface of the final femoral prosthesis component.

The following table lists the parts numbers and parts descriptions as used herein and in the drawings attached hereto.

| PARTS LIST | |
|---|---|
| Part Number | Description |
| 1 | knee joint |
| 2 | femur |
| 3 | distal femur |
| 4 | tibia |
| 5 | proximal tibia |
| 6 | drill bit |
| 7 | drill motor |
| 8 | intramedullary canal |
| 9 | femoral sizer |
| 10 | femoral cutting block |
| 11 | cutting block |
| 12 | upper planar surface |
| 13 | lower planar surface |
| 14 | anterior surface |
| 15 | posterior surface |
| 16 | side wall |
| 17 | side wall |
| 18 | internal A/P slot |
| 19 | anterior cutting guide slot |
| 20 | anterior cutting guide slot |
| 21 | posterior cutting guide slot |
| 22 | posterior cutting guide slot |

PARTS LIST

| Part Number | Description |
| --- | --- |
| 23 | anterior chamfer cutting guide slot |
| 24 | anterior chamfer cutting guide slot |
| 25 | posterior chamfer cutting guide slot |
| 26 | posterior chamfer cutting guide slot |
| 27 | bone spike |
| 28 | spike support |
| 29 | spike support |
| 30 | valgus module |
| 31 | opening |
| 32 | opening |
| 33 | opening |
| 34 | opening |
| 35 | intramedullary rod |
| 36 | knurled knob |
| 37 | opening |
| 38 | opening |
| 39 | threaded hole |
| 40 | axis |
| 41 | cut |
| 42 | cut |
| 43 | cut |
| 44 | cut |
| 45 | cut |
| 46 | sleeve |
| 47 | threaded portion |
| 48 | unthreaded portion |
| 49 | open ended bore |
| 50 | bushing |
| 51 | internally threaded bore |
| 52 | annular groove |
| 53 | lock ring |
| 54 | washer |
| 55 | sleeve |
| 56 | open center |
| 57 | annular shoulder |
| 58 | opening |
| 59 | slot |
| 60 | slot |
| 61 | appendage |
| 62 | flat surface |
| 63 | appendage |
| 64 | flat surface |
| 65 | feeler gauge |
| 66 | support block |
| 67 | pointer arm |
| 68 | pointer |
| 69 | longitudinal slot |
| 70 | peripheral shoulder |
| 71 | flat surface |
| 72 | bolt |
| 73 | plate |
| 74 | threaded section |
| 75 | annular groove |
| 76 | retaining ring |
| 79 | opening |
| 80 | rectangular slot |
| 81 | flat surface |
| 82 | side wall |
| 83 | side wall |
| 84 | opening |
| 85 | transverse shoulder |
| 86 | lock pin |
| 87 | opening |
| 88 | flat underside |
| 90 | posterior referencing paddle |
| 91 | flange |
| 92 | flange |
| 93 | gap |
| 94 | post |
| 95 | post |
| 96 | base |
| 97 | flat surface |

PARTS LIST

| Part Number | Description |
| --- | --- |
| 98 | appendage |
| 99 | appendage |
| 100 | space |
| 101 | distal cutting block |
| 102 | set screw |
| 103 | set screw |
| 104 | slot |
| 105 | slot |
| 106 | flat surface |
| 107 | flange |
| 108 | flange |
| 109 | cone-shaped end |
| 110 | trial prosthesis |
| 111 | articulating surface |
| 112 | non-articulating surface |
| 113 | insert |
| 114 | cutting guide surface |
| 115 | cutting guide surface |
| 116 | V-shaped recess |
| B | cutting blade |
| C | cutting instrument |
| D | slot thickness |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A distal femoral cutting block apparatus comprising:

a) an instrument body having generally flat opposing anterior and posterior surfaces and generally flat proximal and distal surfaces, the distal surface providing a femoral engaging surface;

b) a plurality of generally flat peripheral surfaces on the instrument body including anterior and posterior surfaces and medial and lateral surfaces;

c) a transverse slot extending along a line that approaches each of the opposing anterior and posterior surfaces;

d) a valgus module slidably disposed in the slot, the module comprising in part a tubular member having an open ended bore that extends through the tubular member;

e) the instrument body having a pair of diagonally extending slots that communicate with each of the opposing proximal and distal surfaces, the diagonally extending slots intersecting near the distal surface of the instrument body and about halfway in between the anterior and posterior surfaces of the instrument body;

f) each diagonal slot forming an acute angle with the proximal and distal surfaces of the instrument body;

g) the instrument body having a pair of slots respectively adjacent the anterior and posterior surfaces;

h) an intramedullary rod that fits the open ended bore of the module; and i) a holder for securing the module to the block in a desired position along the length of the slot.

2. The cutting block apparatus of claim 1 wherein the block body is generally rectangular, having a pair of generally flat opposing parallel proximal and distal surfaces and a plurality of generally flat peripheral surfaces, wherein the peripheral surfaces are perpendicular to the parallel proximal and distal surfaces and wherein each peripheral surface forms a generally right angle with the adjoining peripheral surface.

3. The cutting block apparatus of claim 1 wherein the tubular member bore has an axis that forms an acute angle with the femoral engaging surface.

4. The cutting block apparatus of claim 1 wherein the tubular member is generally cylindrically shaped, having an externally threaded portion.

5. The cutting block apparatus of claim 1 wherein the block body has proximal and distal parallel flat surfaces and the open ended bore of the module has a central longitudinal axis that forms an acute angle with each of the proximal and distal parallel flat surfaces.

6. The distal femoral cutting block of claim 5 wherein the holder includes a lock nut having an internally threaded bore that engages a correspondingly threaded section of the valgus module.

7. The distal femoral cutting block of claim 1 wherein the transverse slot is generally perpendicular to the anterior and posterior peripheral surfaces.

8. The distal femoral cutting block of claim 1 wherein the transverse slot has a central axis parallel to at least two of the peripheral surfaces.

9. The apparatus of claim 1 wherein the tubular member has an upper end portion, that carries a knob that defines an actuator for the locking means.

10. The surgical cutting block of claim 1 further comprising bone spike receptive openings on the instrument body for enabling a surgeon to affix the instrument body to a patient's distal femur using bone spikes.

11. A surgical cutting block for preparing a patient's distal femoral bone tissue to receive a femoral knee implant, comprising:

a) a cutting block body having upper and lower generally parallel surfaces, and anterior and posterior planar, generally parallel surfaces that are each generally perpendicular to the upper and lower surfaces;

b) anterior and posterior cutting guide slots defining anterior and posterior cutting guides adjacent to the anterior and posterior surfaces;

c) a pair of diagonally extending cutting guide slots positioned between the anterior and posterior slots and defining cutting guides for making chamfer cuts on a patient's leg bone at the knee joint;

d) the cutting block body including a transverse slot extending between the anterior and posterior surfaces;

e) a valgus module that is movably disposed within the transverse slot between first and second end adjustment positions and intermediate adjustment positions therebetween, for angling the upper and lower surfaces relative to the patient's valgus angle;

f) the valgus module including an open ended bore for receiving a rod, the bore having a central axis that forms an angle with the upper and lower surfaces of the cutting block; and g) a locking member carried by the valgus module for affixing the module to the cutting block at a desired of said adjustment positions along the slot by engaging the upper surface wherein the locking member travels with the valgus module.

12. The apparatus of claim 11 wherein the valgus module comprises a module member having a shaped external surface area that conforms to the shape of the slot so that the module member slides in the slot.

13. The apparatus of claim 11 further comprising anterior referencing feeler gauge means removably attachable to the cutting block body for referencing the block body position to the patient's anterior femoral cortical surface.

14. The apparatus of claim 11 further comprising posterior referencing paddle means removably attachable to the cutting block body for referencing the cutting block body position to the patient's posterior femoral cortical surface.

15. The apparatus of claim 11 wherein the valgus module comprises a sliding member mounted in the transverse slot, a hollow member that forms a removable connection with the sliding member, a bushing that surrounds the hollow member, said bushing having angled surfaces that engage the cutting block body at the transverse slot.

16. The surgical cutting block of claim 11 further comprising bone spike receptive openings on the cutting block body for enabling a surgeon to affix the cutting block body to a patient's distal femur using bone spikes.

* * * * *